(12) United States Patent
Sundholm et al.

(10) Patent No.: US 7,108,867 B2
(45) Date of Patent: Sep. 19, 2006

(54) PROCESS FOR PREPARING PARTICLES

(75) Inventors: Goran Eric Sundholm, Sodertalje (SE); Mustafa Demirbuker, Solna (SE); Saeed Moshashaee, Indianapolis, IN (US)

(73) Assignee: Astrazeneca AB, Sodertalje (SE)

( * ) Notice: Subject to any disclaimer, the term of this patent is extended or adjusted under 35 U.S.C. 154(b) by 449 days.

(21) Appl. No.: 10/250,868

(22) PCT Filed: Jan. 21, 2002

(86) PCT No.: PCT/GB02/00261

§ 371 (c)(1),
(2), (4) Date: Jul. 8, 2003

(87) PCT Pub. No.: WO02/058674

PCT Pub. Date: Aug. 1, 2002

(65) Prior Publication Data

US 2004/0058007 A1    Mar. 25, 2004

(30) Foreign Application Priority Data

Jan. 26, 2001    (GB)    ................................ 0102075.9

(51) Int. Cl.
*A61K 9/14* (2006.01)
*A61K 9/16* (2006.01)
*A61K 38/00* (2006.01)
*A61K 38/28* (2006.01)
*B01J 13/00* (2006.01)

(52) U.S. Cl. ...................... 424/490; 424/489; 424/491; 424/497; 424/499; 514/2; 514/3; 514/4; 514/170; 514/171; 514/172; 514/174; 514/182; 514/613; 514/625

(58) Field of Classification Search ........ 424/489–491, 424/497, 499; 514/2–4, 170–172, 174, 182, 514/613, 625
See application file for complete search history.

(56) References Cited

U.S. PATENT DOCUMENTS

| 5,346,702 | A | 9/1994 | Na et al. ...................... 424/490 |
| 5,639,441 | A | 6/1997 | Siever et al. ................. 424/9.3 |
| 6,299,906 | B1 | 10/2001 | Bausch et al. .............. 424/489 |
| 2005/0181041 | A1* | 8/2005 | Goldman .................... 424/456 |
| 2006/0029676 | A1* | 2/2006 | Sun ............................. 424/489 |

FOREIGN PATENT DOCUMENTS

| EP | 0677332 | 10/1995 |
| WO | 9013285 | 11/1990 |
| WO | 9501221 | 1/1995 |
| WO | 9600610 | 1/1996 |
| WO | 9714407 | 4/1997 |
| WO | 9836825 | 8/1998 |
| WO | 9944733 | 9/1999 |
| WO | 9952507 | 10/1999 |
| WO | 9959710 | 11/1999 |
| WO | 0030613 | 6/2000 |
| WO | 0037169 | 6/2000 |
| WO | 0103821 | 1/2001 |
| WO | 0115664 | 3/2001 |

OTHER PUBLICATIONS

Winters et al., Precipitation of Proteins in Supercritical Carbon Dioxide, 1996, J. Pharm Sci, 85, 586-594.

Jackson et al., Beware of Proteins is DMSO, Biochem et Biophysica Acta 1078, 231-235 1991.

Bertucco A., (1999) Precipitation and Crystallisation Techniques, Chemical Synthesis Using Supercritical Fluids, El. Jessor, P.G., 108-126.

Bleich, J. et al., (1993) Aerosol Solvent Extraction System—A New Microparticle Production Technique, Int. J. Pharm., 97, 111-117.

Blohm, D. et al., (1998) Pharmaceutical Proteins, Angew. Chem., Intl. Ed. Engl. 27, 207-225.

Dixon, D.J. et al. (1993) Polymeric Materials Formed by Precipitation with a Compressed Fluid Antisolvent, AIChE Journal, 39, 127-139.

Donsi, G. et al., Micronization by Means of Supercritical Fluids: Possibility of Application to Pharmaceutical Field, Pharm. Acta Helv., 66, 170-173 1991.

Kikic, I. et al. (1998) Application of Supercritical Fluids to Pharmaceuticals: Controlled Drug Release Systems, Second NATO-ANSI-On Supercritical Fluids: Fundamentals and Applications, Kemer, Turkey, Jul. 1998, 291-306.

Mawson, S. et al. (1991) Stabilized Polymer Microparticles by Precipitation with a Compressed Fluid Antisolvent. 1. Poly(fluoroacrylates), Macromolecules, 30, 71-77.

Moshashaee, S. et al., (2000) Supercritical Fluid Processing of Proteins I: Lysozyme Precipitation From Organic Solution, E.J. Pharm. Sci. 11, 239-245.

Palakodaty, S., et al. (1999) Phase Behavioral Effects on Particle Formation Processes Using Supercritical Fluids, Pharm. Res., 16, 976-985.

(Continued)

*Primary Examiner*—John Pak
(74) *Attorney, Agent, or Firm*—White & Case LLP

(57) ABSTRACT

A process for preparing particles of a substance, such as a protein or polypeptide, comprising: (a) preparing a first liquid comprising water, the substance and a modulator, wherein the modulator has a solubility in water which decreases with increasing temperature; and (b) contacting the first liquid with a second liquid comprising a fluid gas and an organic solvent using an anti-solvent fluid gas technique under conditions of temperature and pressure which result in the precipitation of particles comprising the substance, wherein the temperature of the first liquid is at or above the cloud point temperature of the first liquid when the first liquid contacts the second liquid. Also claimed are particles obtained according to the process and compositions containing the particles.

17 Claims, 4 Drawing Sheets

OTHER PUBLICATIONS

Palakodaty, S. et al. Particle Formation using Supercritical Fluids-A Novel Approach, Proceedings, 1997 IChemE Jubilee Research Event, 501-504 1997.

Sarup, L. et al. (2000) Investigation of Supercritical Fluid Technology to Produce Dry Particulate Formulations of Antibody Fragments, Trans IChemE, 78, part C, 101-104.

Sloan, R. (1998), in Proceeding of the 5$^{th}$ Meeting on Supercritical Fluids, Nice, France, Tome 1, 301-306.

Sloan, R. et al. (1999) in Proceeding of the 6$^{th}$ Meeting on Supercritical Fluids-Chemistry and Materials, Nottingham, UK, 169-174.

Subramaniam, B. et al., (1997) Pharmaceutical Processing with Supercritical Carbon Dioxide, J. Pharm. Sci., 86, 885-890.

Tom, J. et al., (1993) Applications of Supercritical Fluids in the Controlled Release of Drugs, Supercritical Engineering Science, American Chemical Society, 240-257.

Yeo, S.D. et al. (1993) Formation of Microparticulate Protein Powders Using a Supercritical Fluid Antisolvent, Biotechnol. Bioeng. 41, 341-346.

York, P. Strategies for Particulate Design Using Supercritical Fluid Technologies, PSTT, vol. 2, No. 1, Nov. 1999, 430-440.

Chemical Abstracts, 126:187774, Apr. 7, 1997, Columbus, Ohio.

* cited by examiner

PROCESS FOR PREPARING PARTICLES

PROCESS FOR PREPARING PARTICLES

This application is a 371 of PCT/GB02/00261, filed on Jan. 22, 2002.

FIELD OF THE INVENTION

The present invention relates to a process for preparing particles of a substance using an anti-solvent technique working under supercritical or subcritical conditions, more particularly to a process for preparing particles having a diameter of less than 10 microns of a protein or polypeptide using the solution enhanced dispersion by supercritical fluids (SEDS) process.

BACKGROUND OF THE INVENTION

Supercritical fluids have unique properties, since they combine liquid-like solvent power with gas-like transport properties. They have a large compressibility compared to ideal gases. Therefore, a small change in temperature or pressure near the critical values will result in large changes in the fluid's density and hence its solvent power. These characteristics can be utilised to provide highly controllable solvation properties.

Carbon dioxide is the most widely used supercritical fluid, due to the favourable critical parameters ($T_c$=31.1° C., $P_c$=73.8 bar), cost and non-toxicity.

Two principles for precipitating particles with supercritical fluids have been developed, Rapid Expansion of Supercritical Solutions (RESS) and Supercritical Anti-solvent (SAS) or Gas Anti-solvent (GAS) precipitation.

In the RESS process the sensitivity of solvent power of a supercritical fluid to small changes in pressure is used to trigger a mechanical precipitation of particles. However RESS is not suitable for use with substances such as peptides and proteins that have low solubility in the supercritical fluid.

The SAS or GAS processes can be used to precipitate particles of a substance that is insoluble in the supercritical fluid, provided that the supercritical fluid is miscible with the liquid in which the substance is dissolved.

WO 95/01221, WO 96/00610, WO 98/36825, WO 99/44733, WO 99/59710, WO 01/03821 and WO 01/15664 describe Solution Enhanced Dispersion by Supercritical fluids (SEDS) processes, which in addition to the anti-solvent properties of the supercritical fluid, has coupled a physicomechanical function. The SEDS technique involves a continuous flow of a solution containing the substance to be precipitated and the supercritical fluid, co-introduced through a coaxial nozzle into a particle-formation vessel which leads to substantially simultaneous dispersion and mixing of the solution, rapid supersaturation and particle nucleation and formation. By varying the process conditions used in the SEDS process the properties of the resulting particles can be controlled.

Precipitation of proteins using supercritical carbon dioxide has to date mainly been limited to dissolving the proteins in organic solvents such as dimethylsulfoxide (DMSO) and N,N-dimethylformamide (DMF). However, the use of such solvents to dissolve the protein can result in unfolding or denaturing of the protein. This can give rise to a loss in therapeutic effect (Winters et al, Precipitation of Proteins in Supercritical Carbon Dioxide, 1996, J. Pharm Sci, 85, 586–594, Jackson et al, Beware of Proteins in DMSO, Biochem et Biophysica Acta 1078, 231–235).

Furthermore, the rapid extraction of the organic solvent by the supercritical fluid tends to promote agglomeration of the particles as they precipitate from the solution due to the rapid nucleation and particle growth.

The precipitation of proteins from an aqueous solution would avoid damage to the protein caused by the presence of organic solvents such as DMSO. However the poor solubility of supercritical carbon dioxide in aqueous solutions and vice versa is a major hindrance to using anti-solvent techniques such as SEDS™ with aqueous solutions of many substances such as proteins. The use of anti-solvent techniques such as SEDS™ to precipitate particles from an aqueous solution results in the formation of large particles compared to precipitation from solvents such as DMSO. The formation of large particles is undesirable when, for example, the precipitated particles will be used as a pulmonary medicament which is inhaled by patients. In such cases the particles preferably have a particle diameter of less than 10 microns.

WO 96/00610 discloses the preparation of protein particles from a solution of the protein in water and ethanol using the SEDS technique. In WO 96/00610 a three-channelled co-axial nozzle is used to mix an aqueous solution of the protein with the ethanol just prior to dispersion in supercritical carbon dioxide. It is thought that the presence of ethanol improves the solubility match between carbon dioxide and water and thereby improves the efficiency of the SEDS process.

WO 99/52507 describes a process for incorporating an active substance in a carrier matrix wherein a stable water-in-oil emulsion is prepared comprising a continuous non-aqueous phase and a discontinuous aqueous phase, the active substance being present in the discontinuous aqueous phase and the carrier being present in either the aqueous phase or the non-aqueous phase. Particles comprising the active substance and carrier are then formed by contacting the stable water-in-oil emulsion with an antisolvent fluid gas using, for example the SEDS technique.

WO 97/14407 describes a process for the preparation of water-insoluble drug particles having an average particle size of from 100 nm to 300 nm by spraying a solution of the drug in an organic solvent into a compressed gas, liquid or super-critical fluid containing a surface modifier dissolved in an aqueous phase. The presence of the aqueous phase is stated to reduce agglomeration of the precipitated particles.

U.S. Pat. No. 6,299,906 describes a process in which a drug is dissolved in compressed dimethylether optionally containing a surface modifier and the resulting solution is sprayed into an anti-solvent.

Although the use of water as a solvent is desirable for many substances such as proteins, traces of water in the precipitated particles can result in the formation of tightly bound particles agglomerates. This is undesirable as such agglomerates are difficult to break up and, in effect, give rise to a large particle size distribution. The formation of tightly bound agglomerates is a particular disadvantage when the particulate product is designed to be used as an inhalable medicament. In these applications the formation of small (preferably sub-micron) particles of a uniform size are required to ensure an accurate dose of the medicament. Thus any particle agglomerates which do form should be loosely bound so that they can be easily broken up prior to administration to a patient (for example through the use of an inhaler). Furthermore, the agglomeration of precipitated particles can cause blockages in the filtration systems used in the SEDS apparatus giving rise to over-pressurisation of the apparatus. The presence of such agglomerates therefore precludes the development of a continuous/extended precipitation process.

The poor solubility of water in super critical fluids such as carbon dioxide also results in a relatively slow extraction of water and therefore a slow precipitation of particles. Such conditions favour the formation of large (>1 μm) particles.

There is therefore a need for a process which enables the formation of particles (especially sub-micron particles of a uniform size) from an aqueous medium which avoids some or all of the difficulties described above.

SUMMARY OF THE INVENTION

According to a first aspect of the present invention there is provided a process for preparing particles of a substance comprising:
(a) preparing a first liquid comprising water, the substance and a modulator, wherein the modulator has a solubility in water which decreases with increasing temperature; and
(b) contacting the first liquid with a second liquid comprising an anti-solvent fluid gas and an organic solvent using an anti-solvent fluid gas technique under conditions of temperature and pressure which result in the precipitation of particles comprising the substance,
wherein the temperature of the first liquid is at or above the cloud point temperature of the first liquid when the first liquid contacts the second liquid.

DETAILED DESCRIPTION OF THE INVENTION

We have surprisingly found that the presence of the modulator in the first liquid provides sub-micron particles of a uniform size. The present process also reduces the formation of tightly bound particle agglomerates compared to processes in which the modulator is absent. The reduction of agglomeration enables the process according to the present invention to be performed as a continuous/extended process by reducing the risk of over pressurisation of the apparatus used in the fluid gas anti-solvent technique caused by, for example, filter blockage by agglomerates. Reduction of the formation of tightly bound agglomerates is advantageous when the particles are administered to a patient by inhalation, because it is easier to accurately control the dose provided and the reduced agglomeration gives improved dispersion of the particles into the lung.

Preferably the particles have a mass median diameter (MMD) of less than 10 μm, more preferably less than 1 μm especially from 100 to 900 nm and still more especially from 200 to 500 nm. The MMD may be determined using methods well known in the art, for example using an LS Coulter particle size analyser.

The particles may be in a crystalline, semi-crystalline or amorphous form.

The particles prepared by the process according to the present invention are of a uniform size. Thus the particles generally exhibit a narrow particle size distribution.

Modulator

The modulator has an aqueous solubility (s) that decreases when the temperature (T) increases i.e. $ds/dT<0$. In particular the aqueous solubility of the modulator decreases with temperature over the operating temperature of the process according to the present invention. Accordingly, suitable modulators are those which have an aqueous solubility which decreases as the temperature increases in the range of from approximately 10° C. to the temperature of the second liquid used in step (b) of the process. The temperature of the second liquid in step (b) will depend upon the particular anti-solvent fluid gas and the anti-solvent technique employed. When carbon dioxide is the anti-solvent fluid gas and is used in a supercritical state, the modulator preferably has a solubility in water which decreases as the temperature increases from 10 to 60° C., more preferably from 30 to 50° C.

The first liquid comprising water, the substance and the modulator has a cloud point temperature which is below or at the temperature at which the first liquid is contacted with the second liquid used in step (b) of the process according to the present invention.

The cloud point temperature is the temperature at which a solution containing the modulator undergoes a phase separation caused by the modulator becoming insoluble as the temperature of the solution increases. At the cloud point temperature a solution of the modulator will become cloudy due to phase separation of the modulator from the solution. In the case of the modulators suitable for use in the present process the cloud point will typically be at a temperature which is higher than that used to prepare the first liquid. Accordingly, the modulator will initially be dissolved in the first liquid, however, upon heating the first liquid and prior to contact with the second liquid in, step (b) of the process the first liquid will become cloudy as its temperature exceeds the cloud point because the $ds/dT$ of the modulator is <0 and phase separation of the modulator from the first liquid occurs. Upon phase separation the first liquid comprises a continuous aqueous phase containing the substance, within said continuous aqueous phase are dispersed discrete regions of modulator. It is the presence of the discrete regions of modulator in the continuous aqueous phase that result in clouding of the first liquid.

The cloud point temperature of the first liquid may be determined using routine techniques. For example, a sample of the first liquid may be placed in a suitable glass vessel and the solution gradually heated (for example at 5° C./min). The sample is observed during heating and the cloud point is the temperature at which the solution starts to become turbid or "cloudy". The observation may be performed by eye or, alternatively using a suitable monitoring apparatus, for example by monitoring light transmission through the sample, or by laser scattering. The determination of cloud point temperature may be performed on a small sample of the first liquid by, for example heating a capillary tube containing a sample of the first liquid on a heated stage of a microscope whilst observing the liquid during heating through a microscope.

Without wishing to be bound by theory, it is thought that the phase separation resulting from heating the first liquid to a temperature which is at or above the cloud point temperature results in the formation of regions of modulator rich phase in the continuous aqueous phase containing the substance in the first liquid. Upon contact with the second liquid it is thought that the presence of the modulator rich phases increases surface contact between the second liquid and the aqueous phase containing the substance, thereby promoting the formation of small aqueous sub-units containing the substance, from which particles of the substance are precipitated by extraction of water into the second liquid.

Suitably the modulator is selected from a trialkylester of citric acid, a water-soluble polymer and a surfactant, each of which exhibits a $ds/dT<0$. Suitable water-soluble polymers include water-soluble polyethers, for example polyethylene oxide (PEO), polypropylene oxide (PPO) or copolymers thereof; or water-soluble non-ionic cellulose ethers, particularly ethoxylated or propoxylated cellulose ethers for example ethylmethylcellulose (EMC), hydroxyethylcellulose (HEC), ethylhydroxymethylcellulose (EHMC), ethylhydroxyethylcellulose (EHEC), hydroxymethylcellulose (HMC), hydroxypropylcellulose (HPC) and hydroxypropylmethylcellulose (HPMC).

The term "water-soluble" used herein in reference to the modulator refers to a modulator having a solubility in water at 25° C. of at least 1 mg/ml Suitable surfactants include non-ionic polymeric or oligomeric surfactants which contain ethylene oxy groups, such as non-ionic cellulose-ethylene oxide type surfactants which contain (ethylene oxide) oligomers. Suitable non-ionic surfactants containing ethylene-oxy include those containing, for example from 1 to 100 ethylene-oxy groups or chains. Generally surfactants with shorter ethylene-oxy chain lengths of for example, from 4 to 8 ethylene-oxy groups are preferred because solutions containing these have cloud point temperatures in the region of from 25 to 80° C. The surfactant may also comprise other alkylene-oxy groups, for example propylene-oxy groups or chains. However, generally the ethylene-oxy groups will comprise at least 50% by weight, more preferably at least 80% by weight of the surfactant.

Other suitable surfactants and water-soluble polymers which exhibit a ds/dT<0 are disclosed in "Surfactants and Polymers in Aqueous Solution", Jönsson, B. Lindman, B. Holmberg, K. and Kronberg, B, (1998) John Wiley & Sons Ltd, UK.

Preferably the modulator is a trialkylester of citric acid. The trialkylester is preferably an ester formed between citric acid and an alkanol, preferably a $C_{1-6}$-alkanol, more preferably a $C_{1-4}$-alkanol or especially a $C_{2-3}$-alkanol. The alkanol may be a straight chain, branched chain or cyclic alkanol, for example methanol, propanol, isopropanol, cyclohexanol or (especially) ethanol. Optionally the hydroxy group of the trialkylester of citric acid may be esterified with a suitable carboxylic acid, for example acetic acid. It is especially preferred that the modulator is triethylcitrate.

Mixtures of modulators may be used in the first liquid provided that the first liquid exhibits a cloud point temperature.

Suitably the first liquid has a cloud point temperature in the range of from 25 to 60° C., such as from 25 to 50° C. because this enables the process to be operated under relatively mild conditions, thereby enabling the present process to be used to prepare particles of substances that are sensitive to high temperatures, for example certain proteins or compounds that degrade when exposed to heat.

The amount of modulator present in the first liquid may be varied over wide limits, for example the weight ratio of modulator to substance may be from 50:1 to 1:200, preferably from 50:1 to 1:50. The concentration of modulator used will, necessarily, depend upon the properties of the modulator and the substance in the first liquid.

In one embodiment of the present invention the modulator (particularly triethyl citrate) is present in the first liquid at an equal or higher concentration than the concentration of the substance. For example the weight ratio of modulator to substance may be from 1:1 to 10:1, such as from 1:1 to 5:1, suitably from 1:1 to 3:1.

In an embodiment of the present invention the modulator is soluble in the second liquid, because we have found that this enables the modulator to be extracted from the first liquid upon contact with the second liquid, thereby producing particles of the substance that are substantially free of the modulator (for example containing less than 1% by weight of modulator, suitably less than 0.5% and preferably less than 0.1% by weight of the modulator).

The term "soluble in the second liquid" refers to the modulator having a solubility in the second liquid at the operating conditions of the process in step (b) of at least 0.003 parts per part of second liquid, for example at least 0.05 parts per part of second liquid, such as at least 0.01 parts per part of second liquid wherein parts are by weight. In this embodiment it is preferred that the modulator has a solubility in the second liquid that is equal to, or preferably higher than, the solubility of water in the second fluid at the operating conditions of step (b) of the process. We have found that this ensures substantially all of the modulator is extracted together with the water into the second liquid.

In this embodiment it is preferred that the molecular weight of the modulator (for example water-soluble polymer or non-ionic surfactant) is less than 1000. We have found that modulators with a molecular weight of less than 1000 generally have better solubility in the anti-solvent fluid gas, thereby reducing the amount of modulator present in the particles of the substance.

Preferably the substance is substantially insoluble in the modulator, because this reduces the possibility of the substance being extracted into the second liquid upon contact of the first liquid with the second liquid. By "substantially insoluble" is meant that the substance has a solubility in the modulator at the operating conditions of step (b) of the process, of less than 0.001 parts per part of second liquid, for example at less than 0.0001 parts per part of modulator, wherein parts are by weight.

We have found that when the modulator is triethylcitrate it is substantially miscible with certain supercritical fluids such as carbon dioxide (by which is meant that the triethyl citrate is miscible, or substantially miscible in all proportions in supercritical carbon dioxide or that the triethyl citrate has sufficient solubility in the carbon dioxide at the operating conditions to behave as though the two materials were miscible). This results in very rapid extraction of the triethyl citrate from the first liquid and provides sub-micron sized particles of the substance that are substantially free of the triethyl citrate. This embodiment is particularly useful when substantially pure particles of the substance are required.

In another embodiment the modulator is substantially insoluble in the second liquid. By "substantially insoluble" is meant that the modulator has a solubility in the second liquid at the operating conditions of step (b) of the process, of less than 0.001 parts per part of second liquid, for example at less than 0.0001 parts per part of second liquid, wherein parts are by weight.

In this embodiment the insolubility of the modulator in the second liquid promotes the formation of composite particles comprising the substance and the modulator. This embodiment is advantageous when, for example the substance is a pharmacologically active material and the modulator is a non-ionic cellulose ether such as HEC (a useful pharmaceutically acceptable excipient).

Step (b)

Step (b) of the process of the present invention is performed using a fluid gas anti-solvent technique. Suitable fluid gas anti-solvent techniques, include but are not limited to, GAS (Gas Anti-solvent precipitation) as described in, for example, Gallagher et al, Supercritical Fluid Science and Technology, ACS Symp Ser 406, 1989, pp 334; SEDS (a modified version of the GAS technique) ASES (Aerosol Solvent Extraction System), SAS (Supercritical Anti-solvent) as described in Tom, J. W. Lim, G-B. Debenedetti, P. G. and Prud'homme, R. K. (1993) Applications of supercritical fluids in the controlled release of drugs. Supercritical engineering science, *American Chemical society*, 240–256; and PCA (Precipitation with Compressed fluid Anti-solvent) as described in Dixon, D. J. Jonston, K. P. Bodmeier, R. A. (1993) Polymeric materials formed by precipitation with a compressed fluid anti-solvent, AIChE Journal, 39, 127–139.

In a preferred embodiment, step (b) is performed using a SEDS process. When a SEDS process is used an apparatus is employed comprising a particle-forming vessel with means for controlling the temperature and pressure of said vessel, together with a means for co-introduction into said vessel of the second liquid comprising the fluid gas and the organic solvent, and the first liquid, such that dispersion and extraction of water from the first liquid occur substantially simultaneously by the action of the anti-solvent fluid gas. A suitable apparatus for the SEDS process is described in WO 95/01221, WO 96/00610, WO 98/36825, WO 99/44733, WO 99/59710, WO 01/03821 and WO 01/15664 which are hereby incorporated by reference thereto.

Contact between the first liquid and the organic solvent may occur either substantially simultaneously with, or slightly before, dispersion and extraction, by the fluid gas anti-solvent, for example by employing the multichannel co-axial injection apparatus described in WO 96/00 610. Alternatively, the first liquid may be contacted directly with the second liquid comprising the fluid gas anti-solvent and the organic solvent using the apparatus described in FIG. 1 of WO 95/01221. The timing of contact between the first liquid, the organic solvent and the fluid gas anti-solvent will depend on the nature of the substance, and the nature of the desired properties of particulate end product of the process.

When the substance is sensitive to contact with an organic solvent (for example a protein) it is desirable that the first liquid is contacted directly with the second liquid comprising the anti-solvent fluid gas and organic solvent. Alternatively the first liquid may be contacted with the organic solvent immediately before contact with the anti-solvent fluid gas using, for example a multi-channel nozzle described in WO 96/00 610. This minimises the time of contact between the substance and the organic solvent, thereby minimising any degradation of the substance.

The term "fluid gas" used herein refers to a material in its supercritical, and subcritical states as well as compressed gases.

The term "anti-solvent" used herein refers to the substance being substantially insoluble in the anti-solvent fluid gas. Generally it is desirable that the substance has a low solubility in the second liquid to minimise loss of the substance into the anti-solvent fluid gas and organic solvent, this is particularly the case when the substance in a pharmacologically active substance. Suitably the substance has a solubility in the second liquid of less 0.001 parts per part of the second liquid, preferably less than 0.0001 parts per part of second liquid at the operating conditions of step (b) of the process, wherein the parts are parts by weight.

The term "supercritical fluid" used herein refers to a material which is in its supercritical state, namely above its critical pressure ($P_c$) and critical temperature ($T_c$) simultaneously. In practice, the pressure of the fluid is likely to be in the range $(1.01–7.0)P_c$, and its temperature in the range $(1.01–4.0)T_c$.

The term "subcritical fluid" refers to a material that is above its critical pressure and close to its critical temperature. In practice the temperature of a subcritical fluid is likely to be in the range of $0.9T_c$ up to $T_c$.

As will be realised reference to the term "second liquid" as used herein is intended to cover the combination of the fluid gas anti-solvent and the organic solvent. Thus when the anti-solvent fluid gas is in a supercritical state the second liquid will exhibit properties associated with supercritical fluids by virtue of the presence of the supercritical anti-solvent. Accordingly "second liquid" is intended to encompass supercritical fluids, subcritical fluids and compressed gases, depending upon the conditions used in the anti-solvent fluid gas technique adopted in step (b).

Anti-solvent Fluid Gas

The anti-solvent fluid gas is suitably one or more of carbon dioxide, nitrous oxide, sulphur hexafluoride, ethane, ethylene, propane, n-pentane, xenon, chlorotrifluoromethane, a fluorocarbon such as trifluoromethane, tetrafluoroethane and heptafluoropropane, a chlorofluorocarbon compound or nitrogen. The anti-solvent fluid gas is preferably carbon dioxide. It is preferred that the anti-solvent fluid gas is a supercritical fluid, such as supercritical carbon dioxide.

Organic Solvent

The organic solvent is soluble or, preferably, miscible with the anti-solvent fluid gas. The organic solvent is preferably a water-soluble or more preferably a water-miscible organic solvent.

Suitably the organic solvent is selected from one or more of a lower alcohol, a ketone and an ester. Suitable lower alcohols are those containing up to six carbon atoms, for example methanol, ethanol, propanol or isopropanol. Suitable ketones include, for example acetone or methylethyl ketone. Suitable esters include (1–4C)alkyl acetates, for example ethylacetate. A preferred organic solvent is ethanol.

The amount of organic solvent required in the second liquid will depend upon the operating conditions used in step (b) of the process, the particular anti-solvent fluid gas used and the solubility of the water contained in the first liquid in the anti-solvent fluid gas. The organic solvent in the second liquid acts to modify the solvent properties of the anti-solvent fluid gas, thereby enhancing extraction of water from the first liquid by the anti-solvent fluid gas. Some materials are sensitive to contact with organic solvents, therefore, it is generally desirable to that the second liquid should contain the minimum quantity of organic solvent necessary to enable substantially all the water in the first liquid to be extracted by the anti-solvent fluid gas in step (b) of the process. However, the amount of organic solvent should be less than that required to saturate the fluid gas anti-solvent. In an embodiment of the present invention there is a molar excess of organic solvent relative to the amount of water present in the first liquid.

As hereinbefore stated step (b) of the process according to the present invention is carried out under subcritical or, more preferably, supercritical conditions. The precise conditions of operation of step (b) of the process are dependent upon a number of factors, for example the anti-solvent fluid-gas employed. When carbon dioxide is the anti-solvent fluid gas, a suitable pressure is in the range of from about 80 to about 400 bar, suitably in the range of from 100 to 250 bar, preferably in the range of from 110 to 150 bar whilst the temperature may be in the range of from about 35 up to about 80° C., suitably in the range of from 40 to 70° C., preferably in the range of from 45 to 60° C., providing that the operating temperature is at or above the cloud point temperature of the first liquid.

The precipitated particles resulting from step (b) of the process according to the present invention may be collected using conventional means, for example using a filtration system in the particle formation vessel to separate the particles from the fluid gas, water and ethanol.

The reduced agglomeration of particles prepared using the present process means that advantageously the process may be run for an extended time/substantially continuously compared to processes in which no modulator is used because the filtration systems used to collect the precipitated particles do not block as quickly. The time for which the process according to the present invention is operated will depend upon the desired quantity of particles as well as any limitation resulting from filter clogging. Suitable process runs range of from about 5 min up to about 48 hours, suitably from 15 min up to 24 hours, preferably from 30 min up to 12 hours.

In view of the foregoing preferences in a first preferred embodiment of the invention there is provided a process for the preparation of uniform particles of a substance, said particles having a MMD particle size of less than 10 μm, more preferably the particles are sub-micron (i.e. <1 μm MMD) comprising:
(a) preparing a first liquid comprising water, the substance and a modulator, wherein the modulator has a solubility in water which decreases with increasing temperature; and
(b) contacting the first liquid with a second liquid comprising an anti-solvent fluid gas and an organic solvent (preferably a water-miscible organic solvent) using a SEDS process;
wherein:
i) the substance is soluble in water;
ii) the organic solvent is soluble in the anti-solvent fluid gas;
iii) the substance is substantially insoluble in the second liquid (and preferably substantially insoluble in the modulator);
iv) the amount of organic solvent used is less than that required to saturate the anti-solvent fluid gas; and
v) the temperature of the first liquid is at or above the cloud point temperature of the first liquid when the first liquid contacts the second liquid.

In conditions i) and ii) the term "soluble" refers to a solubility at the operating conditions of step (b) of the process of the substance/organic solvent of at least 0.003 parts per part of water/anti-solvent, preferably at least 0.005 parts per part of water/anti-solvent, for example at least 0.001 parts per part of water/anti-solvent, wherein parts are parts by weight.

In condition iii) the term "substantially insoluble" refers to the substance having a solubility in the second liquid at the operating conditions of step (b) of the process of less than 0.001 parts per part of the second liquid, preferably less than 0.0001 parts per part of second liquid, wherein the parts are parts by weight.

Criterion (iv) is essential for avoiding formation of a two-phase system containing supercritical solvent-saturated anti-solvent, e.g. ethanol-saturated carbon dioxide, and a liquid phase containing e.g. water, solvent and dissolved substance.

It is especially preferred that the anti-solvent fluid gas is carbon dioxide which is in a supercritical state, the organic solvent is ethanol and the modulator is triethyl citrate.

The first liquid is at or above the cloud point temperature of the first liquid when the first liquid contacts the second liquid. The first liquid may be heated using any suitable method. For example the liquid may be heated prior to transfer into the second liquid. Conveniently, when the first liquid is introduced into the second liquid by means of a conduit such as a nozzle, the first liquid may be heated by heat conduction from the second liquid as the first liquid is transported through the conduit. This method of heating is particularly suitable when there is a significant difference between the cloud point temperature and the temperature of the second liquid, because this minimises the residence time of the first liquid in the conduit required to ensure that the first liquid is at or above the cloud point temperature when it contacts the second liquid.

The process according to the present invention provides a high yield of sub-micron particles compared to processes carried out without a modulator. Any larger particles (for example with an MMD of more than 10 μm) that may form can be removed using conventional techniques such as sieving.

As hereinbefore described the present invention reduces the formation of tightly bound particle agglomerates. However, when the particles prepared according to the present invention are of a sub-micron size particle-particle attractive forces, such as Van der Waals forces can give rise to the formation of loosely-bound particle agglomerates. However, we have found that any such agglomerates formed are very loosely bound and are easily broken up, for example by suspending the particles in a carrier liquid or by passing the particles through an administration device such as a nebuliser.

In an embodiment of the present invention, the particles produced according to the present process, may be subsequently contacted with a composition comprising a substantially dry anti-solvent fluid gas (which may be in a supercritical or subcritical state) in order to obtain dry particles of the substance. By "substantially dry" is meant a fluid gas containing less than 1%, for example less than 0.1% by weight of water.

In another embodiment of the present invention the particles of the substance are suitably treated with a composition comprising an anti-solvent fluid gas, especially a super critical anti-solvent (for example super critical carbon dioxide), and a second solvent (for example ethanol). A suitable process for the subsequent treatment of the particles is described in WO 2000/30614 which is incorporated herein by reference thereto. The use of such treatment processes enables the physical characteristics of the particles to be modified, for example by modifying the crystalline state of the particles, and/or by forming solvates of the particles. Such treatments can advantageously enhance the stability of the particles.

Substance

In embodiments of the present invention the substance may be suspended in the first liquid. However, it is preferred that the substance is fully dissolved in the first liquid because this provides more uniform particles and promotes the formation of sub-micron particles of the substance. Thus it is preferred that the first liquid is prepared as a single phase solution comprising the substance and the modulator dissolved in the water. The first liquid is therefore preferably prepared as a clear solution. By the term "solution" is meant that the first liquid is a homogenous single phase, namely that the substance and modulator are sufficiently dissolved in the water to give a clear solution. The first liquid may comprise components in addition to the modulator and substance, for example additives to minimise adsorbtion of the substance to process equipment. For example when the substance is albumin it may advantageous to include an additive such as Polysorbate 80 to minimise adsorbtion of the albumin to surfaces of the apparatus used to prepare the particles. Generally it is preferable to select conditions in step (b) of the process that result in substantially all the additive(s) being extracted into the anti-solvent fluid gas to give particles of the substance having a high purity. It is preferred that the first liquid prepared for use in step (a) of the process should be free of water-immiscible liquids such as water-immiscible organic solvents as the presence of such materials may result in the inadvertent extraction and loss of substance when the first liquid is contacted with the second liquid. Furthermore the presence of such water-immiscible liquids could result in degradation of sensitive substances.

The substance may be an organic or inorganic material or a mixture thereof. Preferably the substance is a pharmacologically active substance, a pharmacologically inert material such as an excipient or additive, or a mixture thereof, for example two or more pharmacologically active substances or a mixture of one or more pharmacologically active substance(s) and one or more pharmacologically inert material(s).

Suitable pharmacologically active substances include $\beta_2$-agonists, glucocorticosteroids, anticholinergics, leukotriene antagonists, leukotriene synthesis inhibitors, hormones, proteins and polypeptides, and mixtures thereof Examples of $\beta_2$-agonists suitable for use in the present invention include, without limitation, formoterol (e.g. formoterol fumarate dihydrate), salmeterol (e.g. salmeterol xinafoate), terbutaline (e.g. terbutaline sulfate), salbutamol (e.g. salbutamol sulfate), bambuterol (e.g. bambuterol hydrochloride), rimiterol, fenoterol, reproterol, pirbuterol, bitolterol, clenbuterol, procaterol, broxaterol, picumeterol, mabuterol, isoprenaline, orciprenaline and adrenaline.

The glucocorticosteroid, if used in the invention, is preferably an anti-inflammatory glucocorticosteroid. Examples of such glucocorticosteroids which may be used in the present invention include betametasone, fluticasone (e.g. as propionate), budesonide, tipredane, dexametasone, beclomethasone (e.g. as dipropionate), prednisolone, fluocinolone (e.g. as acetonide), triamcinolone (e.g. as acetonide), mometasone (e.g. as furoate), flumethasone, flunisolide, ciclesonide, deflazacort and cortivazol. Suitable proteins and polypeptides include insulin, interferons, antibodies, calcitonins, vaccines, parathyroid hormones, granulocyte colony-stimulating factors, follicle stimulating protein and the like. Combinations of these, such as a combination of a corticosteroid and a $\beta$-agonist, are also contemplated. Examples of suitable proteins and polypeptides include those which are suitable for administration to a patient by inhalation.

When a mixture of pharmacologically active substances is used, each component of the mixture is dissolved in the first liquid. The resulting solution is then contacted with the second liquid to form particles comprising the pharmacologically active materials. Depending upon the physical properties of the active components and the conditions used in step (b), the resulting particles may comprise a mixture of individual particles of each active substance. Alternatively, the particles may be formed as a composite material wherein each particle comprises a mixture the active components. Suitable mixtures of active substances that may be used include, for example a mixture of a glucocorticosteroid and a $\beta_2$-agonist such as budesonide and formoterol.

When the substance is a pharmacologically inert material it is preferably a pharmaceutically acceptable excipient, such as a carrier, an additive or a diluent, including antioxidants. Suitable pharmaceutically acceptable excipients include, without limitation, monosaccharides e.g. glucose, fructose and galactose), disaccharides (sucrose, trehalose, maltose, cellobiose and lactose, preferably lactose as the monohydrate), trisaccharides (e.g. raffinose, melezitose), oligosaccharides, polysaccharides or polyols. The polysaccharides may be cellulose, starch, dextrins or dextran, or chemical derivatives of any of these. The polyol is preferably a sugar alcohol e.g. sorbitol and mannitol. Suitable additives include those that enhance in-vivo absorption of a drug, for example solubility enhancers.

The hereinbefore mentioned substances may be in the form of pharmacologically acceptable esters, salts, solvates (such as hydrates), or solvates of such esters or salts. The substance may also be in the form of a racemic mixture or as one or more optical isomers.

As hereinbefore mentioned, the substance may comprise a mixture of substances, for example a mixture comprising two or more pharmacologically active substances or a mixture comprising one or more pharmacologically active substance and one or more pharmacologically inert substance.

When the substance is a pharmacologically active substance(s) it may be premixed with one or more pharmaceutically acceptable excipients or additives before the process of the invention is applied (for example by dissolving the pharmacologically active substance(s) and pharmaceutically acceptable excipient/carrier(s) in the first liquid). This is especially advantageous if the active substance is highly potent. The co-precipitation of a pharmacologically active substance and a pharmaceutically acceptable excipient from the first liquid is useful for example, for modifying the dissolution and/or absorption characteristics of the pharmacologically active substance. For example, the substance may comprise insulin and an absorption enhancer such as sodium taurocholate.

Preferably the substance has a solubility in water at 25° C. of more than 1 mg/ml, preferably more than 10 mg/ml and most preferably more than 20 mg/ml.

The amount of material in the first liquid will, necessarily depend upon the properties of the substance. Generally it is desirable that the concentration of the substance in the first liquid is as high as possible whilst maintaining the substance in solution in the first liquid. Suitably the first liquid contains a sufficient amount of the substance to form a saturated or near-saturated solution of the substance in the first liquid as this increases the amount of particles formed per-unit volume of the first liquid According to a second aspect of the present invention there is provided particles of a substance obtained by the process according to the first aspect of the present invention. As hereinbefore described the particles may comprise a single substance, a mixture to two or more substances or a composition comprising particles of the substance and the modulator. The particles may be further formulated to provide compositions as hereinbefore described. For example, a pharmaceutical composition comprising particles of a pharmacologically active agent according to the second aspect of the present invention and one or more pharmaceutically acceptable excipient(s), wherein, optionally, the excipient(s) is prepared using the process according to the first aspect of the present invention.

According to a third aspect of the present invention there is provided a pharmaceutical composition comprising a pharmacologically active substance and a pharmaceutically acceptable excipient, carrier or diluent, wherein at least one of the pharmacologically active substance and pharmaceutically acceptable excipient, carrier or diluent, has been prepared by the process according to the first aspect of the invention.

The pharmaceutical composition may comprise particles comprising a pharmacologically active substance prepared using the process according to the present invention that are mixed with one or more suitable pharmaceutically acceptable excipient(s). In this case, the excipient particles may also be produced according to the present invention using e.g. the SEDS technique, or may be prepared by another suitable technique. It is also possible to prepare particles containing one or more excipient(s) according to the present invention and mix them with particles containing one or more pharmacologically active substance(s). In this case, the particles of an active substance may also be prepared according to the present invention, or may be prepared by another suitable technique.

When the particles and compositions according to the second and third aspects of the present invention comprise a pharmacologically active substance the particles may be used for pharmaceutical purposes including, but not limited to therapeutic and prophylactic treatments and for diagnostic purposes.

When the particles prepared according to the present invention are used for pharmaceutical purposes they may be administered by a variety of routes including but not limited to oral, rectal, tonsillar, buccal, nasal, vaginal, parenteral, intramuscular, subcutaneous, intraoccular, pulmonary or transdermal administration.

As hereinbefore mentioned in a preferred embodiment the particles according to the second aspect of the invention are of a sub-micron particle size comprising a pharmacologically active protein or polypeptide (especially insulin) which is suitable for pulmonary administration.

Such particles, and formulations thereof, may for example, be suitable for use in the treatment of a respiratory disorder such as an allergic and/or inflammatory condition of the nose or the lungs, for the use in the treatment of intestinal disease as inflammatory bowel diseases or for the use in the treatment of diabetes.

The present invention will be illustrated, but not limited by the following examples:

EXAMPLE 1

Example 1.1

Figure 1:
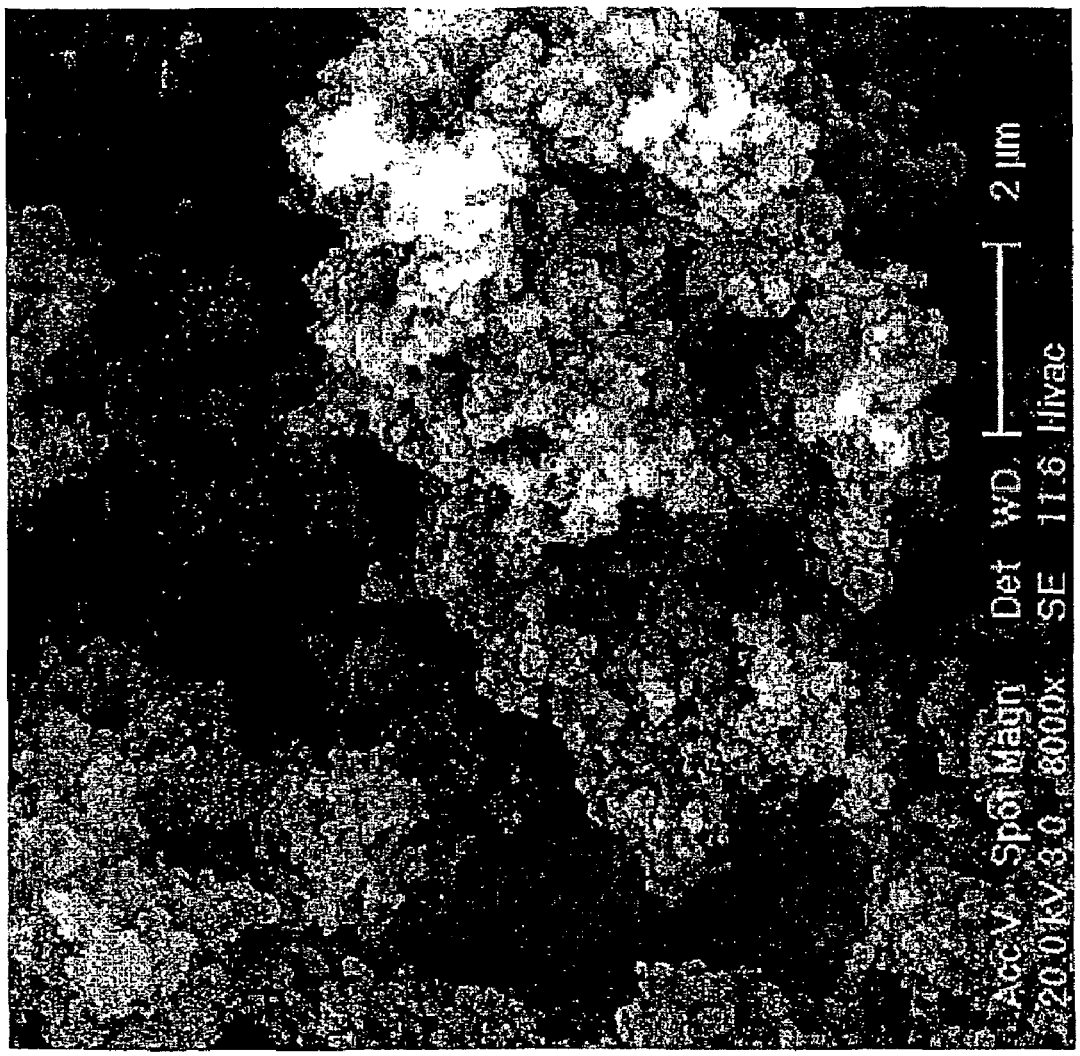
FIG. 1 shows particles of lysozyme precipitated from water using a SEDS process without the presence of a triethyl citrate modulator.

Lysozyme (100 mg, ex Sigma-Aldrich) was dissolved in a solution of 300 mg triethyl citrate in water (5 ml) at ambient temperature (approximately 22° C.). The solubility of triethyl citrate in water at 25° C. is 5.7 g/100 ml This solution is mixed with carbon dioxide modified with ethanol through a coaxial nozzle (nozzle tip diameter 0.1 mm) in the chamber of a SEDS apparatus as described in FIG. 1 and accompanying text in WO 95/01221. The carbon dioxide and ethanol are co-introduced into one channel of the nozzle at the flow rates indicated below. The lysozyme solution was heated to 50° C. giving a cloudy solution (caused by phase separation of the triethyl citrate as the temperature of the solution exceeded the cloud point temperature of the solution). The solution was then introduced into the SEDS particle formation chamber of the apparatus at the flow rate specified below.

The lysozyme particles formed, are collected in the bottom of the chamber. The triethyl citrate is dissolved in the supercritical carbon dioxide and thereby removed, resulting in lysozyme particles that were substantially free of triethylcitrate. The experiment was carried out without noticeable pressure increase.

The running conditions of the SEDS apparatus were:

| | |
|---|---|
| Temperature: | 50° C. |
| Pressure: | 100 bar |
| Flow rate of carbon dioxide: | 10 ml/min |
| Flow rate of the solution: | 0.05 ml/min |
| Flow rate of ethanol: | 1.0 ml/min |

Figure 2:
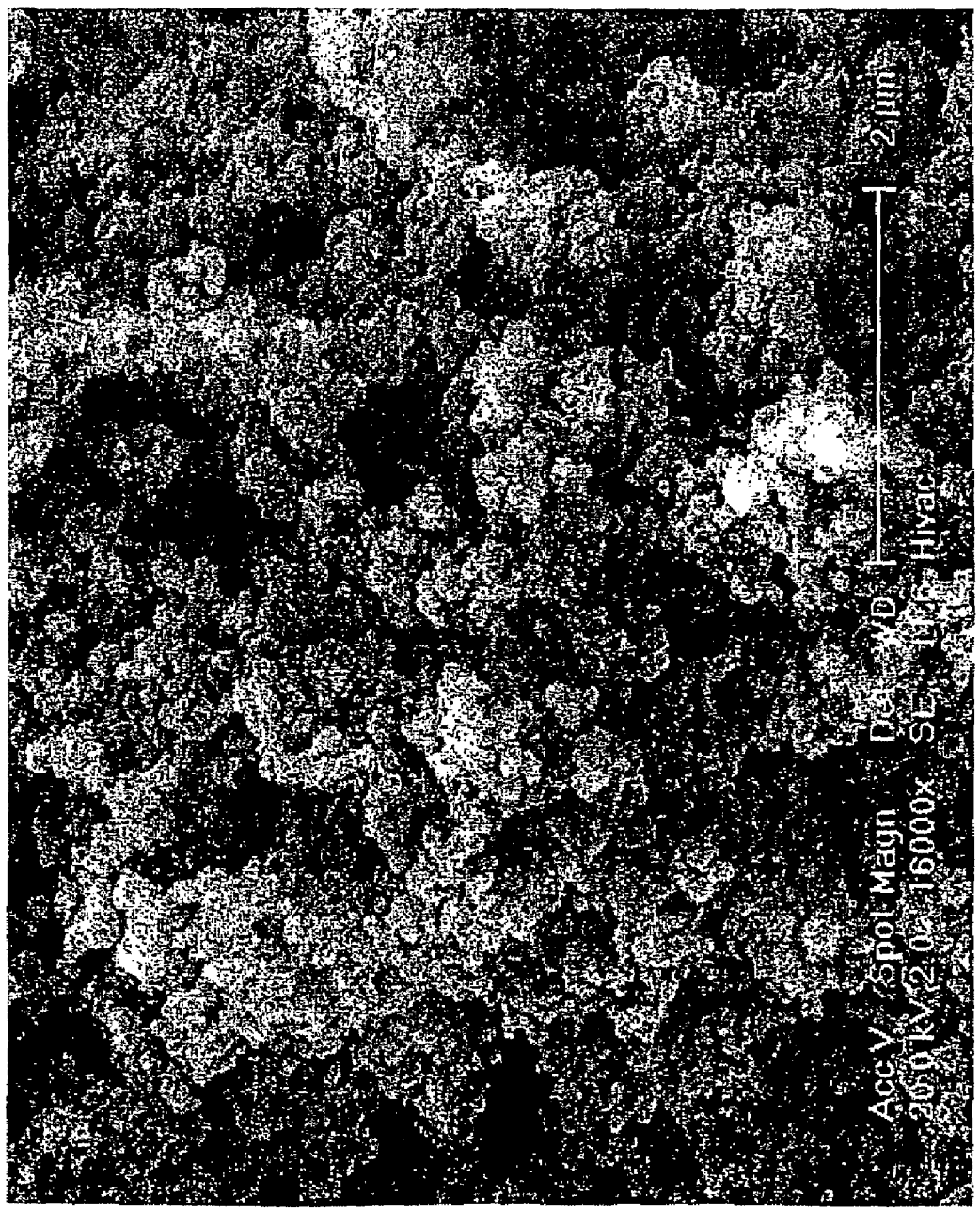
FIG. 2 shows particles of lysozyme precipitated from water using a SEDS process in the presence of a triethyl citrate modulator.

The percentage of lysozyme particles with a MMD of less than 1 micron prepared from the 2% (w/v) lysozyme solution produced was 36%. FIG. 2 is an SEM of the lysozyme particles prepared.

When the process described above was repeated using an aqueous solution in the absence of any triethylcitrate the percentage of particles with a MMD of less than 1 micron was found to be 12% according the LS Coulter particle size measurements.

Example 1.2

Figure 3:
FIG. 3 shows particles of lysozyme prepared precipitated from a water/triethyl citrate solution using a SEDS process in which the second liquid was carbon dioxide and ethanol.

The process described in Example 1.1 was repeated using the following conditions: 90 bar, 50° C., a flow rate of carbon dioxide 9 ml/min, a flow rate of aqueous solution containing lysozyme and triethyl citrate 0.045 ml/min and a flow rate of ethanol 0.9 ml/min. This resulted in lysozyme particles with a MMD of less than 1 micron was 89%. An SEM of these particles is shown in FIG. 3

EXAMPLE 2

5 ml of an aqueous albumin solution containing 10 mg/ml was dissolved in a water solution (5 ml) containing 300 mg triethyl citrate and 200 mg Polysorbate 80 (to minimise adsorption of albumin onto process equipment) (albumin ex. Fluka). The process was carried out as described in Example 1 but with the following operating parameters: temperature 50° C., pressure 200 bar (to ensure full extraction of the Polysorbate 80), a flow rate of carbon dioxide:18 ml/min, a flow rate of the albumin solution 0.08 ml/min and a flow rate of ethanol 1.8 ml/min.

Figure 4:
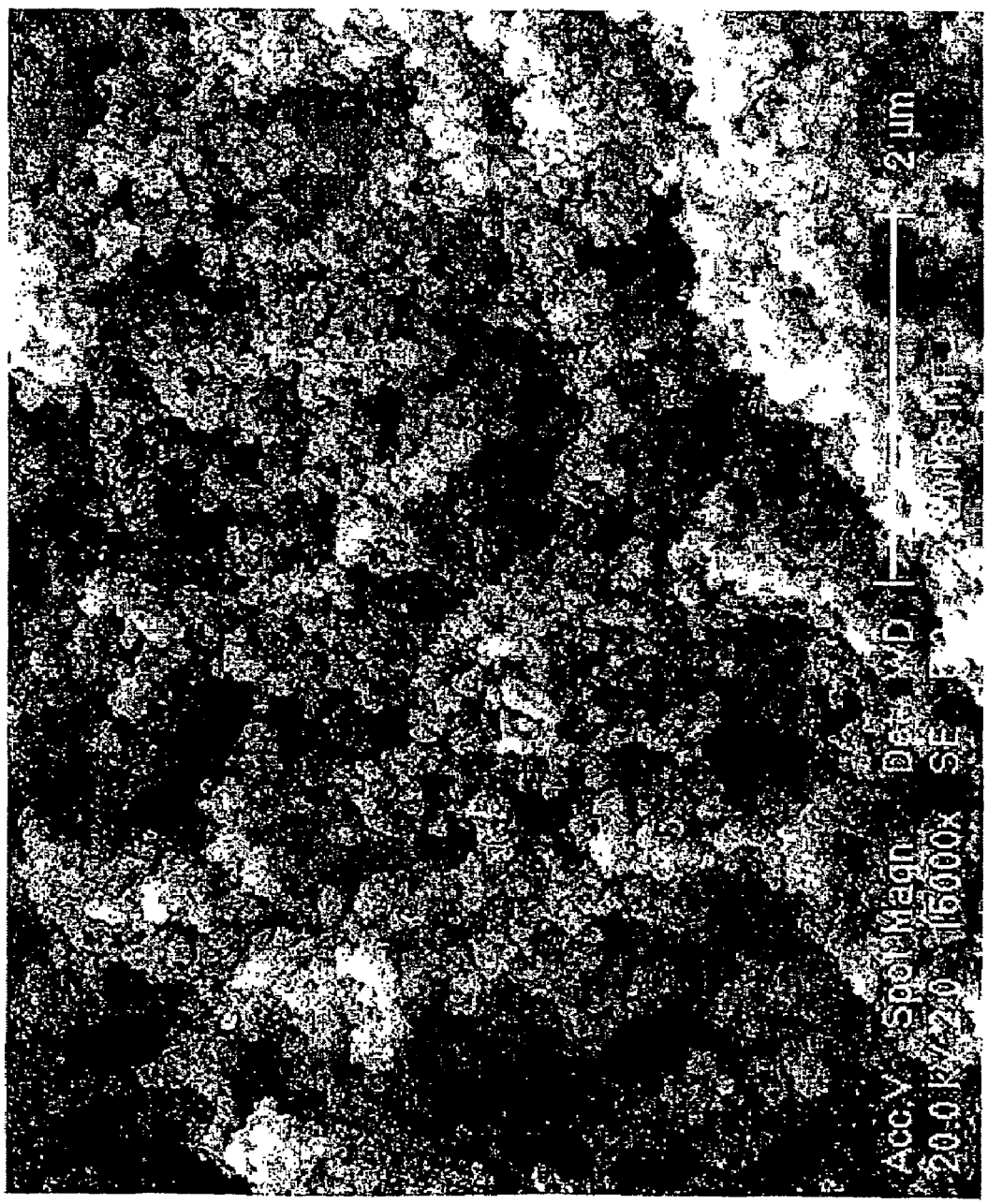
FIG. 4 shows particles of albumin precipitated from water using a SEDS process in the presence of a triethyl citrate modulator.

The SEM analysis in FIG. 4 from this experiment clearly shows the uniform sub-micron particles formed.

EXAMPLE 3

Preparation of Insulin Particles (without Na-taurocholate)

At ambient temperature human insulin (87 mg) was dissolved in 0.02M HCl (2 ml) and 0.02M NaOH (2 ml) and pH was adjusted to pH 7. Triethyl citrate (240 mg) was added and dissolved while stirring. The process was carried out according to Example 1 with the following parameters: temperature 50° C.; pressure 125 bar; flow rate of carbon dioxide: 15 ml/min; flow rate of the insulin solution: 0.05 ml/min and flow rate of ethanol: 1.4 ml/min.

SEM analysis on the resulting particles showed that particles in the range of 0.2 to 2 μm had formed, most particles being of a sub-micron size.

EXAMPLE 4

Preparation of Insulin and Na-taurocholate Particles

At ambient temperature human insulin (345 mg) was dissolved in 0.02M HCl (9 ml) and 0.02M NaOH (9 ml). pH adjusted to 7. Na-taurocholate (115 mg, ex Prodotti Chimici E. Alimentari SPA) was added under stirring triethyl citrate (1.07 g) was added then added. The process was carried out according to Example 1 with the following parameters: temperature 50° C.; pressure 125 bar; flow rate of carbon dioxide: 18 ml/min; flow rate of the insulin solution: 0.05 ml/min and flow rate of ethanol: 2 ml/min.

SEM analysis on the particles showed that particles in the range of 0.1 to 0.5 μm had formed, most particles being of a sub-micron size.

EXAMPLE 5

Preparation of Lysozyme and Na-taurocholate Particles

Lysozyme (153 mg, ex. Serva) was dissolved in water (6 ml) and a solution of Na-taurocholate (15.3 mg, ex Prodotti Chimici E. Alimentari SPA) in water (1.5 ml) was added under stirring, triethyl citrate (450 mg) was then added. The process was carried out according to Example 1 with the following parameters: temperature 50° C.; pressure 100 bar; flow rate of carbon dioxide: 15 ml/min; flow rate of the lysozyme solution: 0.05 ml/min and flow rate of ethanol: 1 ml/min.

SEM analysis showed that uniform sub-micron particles had formed.

The invention claimed is:

1. A process for the preparation of uniform particles of a pharmacologically-active substance, said particles having a mass median diameter of less than 10 microns, the process comprising the steps of:
   (a) preparing a first liquid comprising water, the pharmacologically-active substance and a modulator selected from the group consisting of trialkyl esters of citric acid, wherein the modulator has a solubility in water which decreases with increasing temperature;
   (b) contacting the first liquid with a second liquid comprising an anti-solvent supercritical fluid and an organic solvent using a supercritical anti-solvent technique selected from the group consisting of GAS, SEDS, and SAS;
   wherein:
   i) the pharmacologically-active substance is soluble in water;
   ii) the weight ratio of the modulator to the pharmacologically-active substance present in the first liquid is in the range of from 50:1 to 1:200;
   iii) the organic solvent is soluble in the anti-solvent supercritical fluid;
   iv) the pharmacologically-active substance is substantially insoluble in the second liquid;
   v) the amount of organic solvent used is less than that required to saturate the anti-solvent supercritical fluid and
   vi) the temperature of the first liquid is at or above the cloud point temperature of the first liquid when the first liquid contacts the second liquid; and
   (c) obtaining uniform particles of the pharmacologically-active substance having a mass median diameter of less than 10 microns.

2. The process according to claim 1, wherein the supercritical anti-solvent technique is SEDS.

3. The process according to claim 1, wherein the modulator is triethyl citrate.

4. The process according to claim 1, wherein the pharmacologically-active substance is fully dissolved in the first liquid.

5. The process according to claim 1, wherein the pharmacologically-active substance is a pharmacologically-active protein or polypeptide.

6. The process according to claim 1, wherein the pharmacologically-active substance is insulin.

7. The process according to claim 1, wherein the pharmacologically-active substance comprises two or more substances.

8. Process according to claim 7, wherein the pharmacologically-active substance comprises a glucocorticosteroid and a $\beta_2$-agonist.

9. The process according to claim 8, wherein the pharmacologically-active substance comprises budesonide and formoterol.

10. The process according to claim 7, wherein the pharmacologically-active substance comprises insulin and an absorption enhancer.

11. The process according to claim 10, wherein the pharmacologically-active substance comprises insulin and sodium taurocholate.

12. The process according to claim 1, wherein the cloud point temperature of the first liquid is in the range of from 25° C. to 60° C.

13. The process according to claim 1, wherein the modulator is soluble in the second liquid.

14. The process according to claim 1, wherein the modulator is substantially insoluble in the second liquid.

15. The process according to claim 1, wherein the organic solvent is a water-miscible organic solvent.

16. The process according to claim 15, wherein the organic solvent is ethanol.

17. The process according to claim 1, wherein the first liquid in step (a) is prepared as a single phase solution comprising the pharmacologically-active substance and modulator dissolved in water.

* * * * *

UNITED STATES PATENT AND TRADEMARK OFFICE
CERTIFICATE OF CORRECTION

PATENT NO. : 7,108,867 B2
APPLICATION NO. : 10/250868
DATED : September 19, 2006
INVENTOR(S) : Sundholm et al.

It is certified that error appears in the above-identified patent and that said Letters Patent is hereby corrected as shown below:

On Title page, PCT filing date at item (22)
PCT filing date should read --Jan. 22, 2002--

Signed and Sealed this

Twelfth Day of December, 2006

JON W. DUDAS
*Director of the United States Patent and Trademark Office*